United States Patent [19]

Linnecke et al.

[11] 4,240,751
[45] Dec. 23, 1980

[54] METHOD AND APPARATUS FOR SPECIFIC BINDING SUBSTANCES

[75] Inventors: Carl B. Linnecke, Los Angeles; Daniel Wong, Orange, both of Calif.

[73] Assignee: Akzona Incorporated, Asheville, N.C.

[21] Appl. No.: 959,386

[22] Filed: Nov. 9, 1978

[51] Int. Cl.³ ............................................. G01N 21/27
[52] U.S. Cl. ................................... 356/409; 250/526; 250/227; 356/246; 356/440; 422/102; 435/291; 435/808
[58] Field of Search ............... 250/227, 573-576; 356/409-414, 416, 418, 419, 432, 436, 440, 246; 442/50, 63-68, 99, 102; 435/4, 7, 39, 40, 291, 293

[56] References Cited

U.S. PATENT DOCUMENTS

| | | | |
|---|---|---|---|
| 3,627,432 | 12/1971 | Bergmann | 356/246 |
| 3,628,872 | 12/1971 | Miranda | 250/574 X |
| 3,654,090 | 4/1972 | Schuurs et al. | |
| 3,740,155 | 6/1973 | Keller et al. | 356/246 X |
| 3,791,932 | 2/1974 | Schuurs et al. | 23/230 B X |
| 3,932,763 | 1/1976 | Weinstein | 250/576 |
| 4,016,043 | 4/1977 | Schuurs et al. | |
| 4,075,062 | 2/1978 | Shibata et al. | 356/246 |
| 4,152,075 | 5/1979 | Rellstab et al. | 250/227 |

FOREIGN PATENT DOCUMENTS

| | | |
|---|---|---|
| 1959612 | 6/1971 | Fed. Rep. of Germany ........... 356/432 |
| 2040481 | 2/1972 | Fed. Rep. of Germany . |
| 2451769 | 5/1975 | Fed. Rep. of Germany ........... 356/432 |
| 2320547 | 3/1977 | France ........... 356/432 |

OTHER PUBLICATIONS

Levine et al., *IBM Technical Disclosure Bulletin*, vol. 18, No. 11, Apr. 1976, pp. 3754-3756.

*Primary Examiner*—F. L. Evans
*Attorney, Agent, or Firm*—Robert H. Falk; Charles A. Wendel; Francis W. Young

[57] ABSTRACT

A novel combination and a method are disclosed for detecting and measuring a predetermined substance capable of being specifically bound. The combination comprises a novel adapter which eliminates contact of a light conducting and receiving probe with the sample. The novel combination comprises (1) a fiber optic colorimeter comprising a light source, a means for detecting and measuring light, and a probe containing a plurality of optic fibers including a first light conducting means for conducting light from the light source of the colorimeter to a test sample and a second light conducting means for conducting light from the test sample to the means for detecting and measuring light and (2) a microplate having one or more wells, each of which is adapted to contain a liquid test sample, for use in a predetermined colorimetric medical diagnostic test, wherein a reflective surface is disposed below the bottom of the well of said microplate, said well is adapted to accommodate the probe of said fiber optic colorimeter, and wherein said probe includes an attachment means joinable in a close-fitting engagement with an upper portion of each well in said microplate, the attachment means not engaging said liquid sample. The method of the invention is especially suitable for rapid manual examination of sample wells in microplates.

35 Claims, 12 Drawing Figures

DIFFERENTIATION OF INSTRUMENT RESPONSE CURVES

METHOD AND APPARATUS FOR SPECIFIC BINDING SUBSTANCES

RELATED APPLICATIONS

This application is related by subject matter to U.S. Ser. No. 932,594, filed Aug. 9, 1978, which is a continuation-in-part of Ser. No. 909,862, filed May 26, 1978, both incorporated herein.

BACKGROUND TO THE INVENTION

1. Field of the Invention

The invention relates to the detection and measurement of predetermined substances capable of being bound specifically, using a novel method and combination therefor which provide for rapid qualitative and quantitative determinations in an advantageous manner.

2. Description of the Prior Art and Other Information

Various methods have been developed in the last two or three decades for the determination of a variety of substances capable of being bound specifically, generally immunochemical substances, including antigens, antibodies, haptens, and certain low molecular weight substances. Examples of these methods are:
1. Radioassay techniques
   a. Competitive protein binding assays
   b. Radioimmunoassay (RIA); including competitive, immunoradiometric, sandwich, etc.
2. Fluoroimmunoassays (FIA)
3. Enzyme immunoassay (EIA); including competitive, enzymometric, double antibody solid phase, sandwich, etc.
4. Lysis-initiating immunoassays (LIA)
5. Latex-particle agglutination (LPA)
6. Charcoal-particle agglutination (CPA)
7. Hemagglutination and Hemagglutination Inhibition Assays (HA), (HIA)
8. Complement Fixation (CF)
9. Counter-immunoelectrophoresis (CIEP)
10 Radial Immunodiffusion and Double Diffusion (RID)
11. Viroimmunoassay (VIA); and
12. Spin immunoassay (SIA) among others.
13. Turbidity (physical assay)

One type of immunochemical test system involves the use of labels: e.g. radioisotopes, enzymes, fluorescent labels, etc. Within these, there are many types of labels useful in assays for the detection and measurement in serum or other media or biologically important or interesting compounds or substances. The administration of most of these tests are hampered by one or more of the following limitations: (1) lack of sensitivity, (2) complexity of the test procedure, (3) instability of reagents, (4) hazardous reagents, (5) impure reagents, and (6) expensive equipment required to perform quantitative and qualitative analysis of the amount of label involved in an immunochemical reaction. For a review of the development and evaluation of immunological methods and their uses as diagnostic tools, reference is made to "Immunology as a Laboratory Tool", by FRANZ PEETOOME, *American Journal of Technology*, 37(2), pp. 445-469 (1971), incorporated herein.

There are other immunochemical test systems which do not use labels for a means of detection; some of these are the so-called "agglutination" tests, wherein the analysis depends on the measurement of certain electromagnetic radiation properties of the liquid samples containing immunochemical constituents, with the measured properties depending on whether or not an immunochemical reaction has taken place. A pioneer reference in this area of technology is Schuurs, U.S. Pat. No. 3,551,555 (1970). See also Price et al, U.S. Pat. No. 4,066,744 (1978); both patents are incorporated herein by reference. Examples of these "agglutination" tests include the so-called "NOSTICON" latex tests by Organon Incorporated (West Orange, N.J.), including PREGNOSTICON®, RHEUMANOSTICON®, AND GONOSTICON® latex agglutination or latex agglutination inhibition slide and DRI-DOT® Tests (distinguishable from the "NOSTICON" erythrocyte agglutination inhibition tests).

Both labeled and unlabeled immunochemical testing may employ various devices to separate immunochemical constituents which have reacted from non-reacted immunochemical constituents and from substances irrelevant to the test. For example, some EIA patents require separation through the use of one component in the antigen-antibody reaction being in an "insolubilized" phase for separation—see Schuurs and co-workers in U.S. Pat. Nos. 3,654,090; 3,791,932; 3,850,752; 3,839,153; 3,879,262; 4,016,043 and U.S. Pat. No. Re. 29,169.

Another method does not require separation of free and bound label because the assay depends on the inhibition or activation of the enzymelabel by antibody binding (e.g., the EMIT type system of Syva Corporation of Palo Alto, CA, for EIA and FRAT, or "free radical assay technique", for SIA)—see U.S. Pat. Nos. 3,880,715; 3,852,157; 3,875,011; 3,935,074; and 3,905,871, and an article by Kenneth S. Rubenstein et al in "Homogenous Enzyme Immunoassay, a New Immunochemical Technique", *Biochemical and Biophysical Research Communications* 47, No. 4, 846-851 (1972) (all incorporated herein by reference). There are examples wherein an insolubilized phase is not employed and the assay depends on inhibition or activation of the enzyme label by antibody binding. See also G. Brian Wisdom, "Enzyme Immunoassay", *Clinical Chemistry* 22/8, 1243 (1976).

Radioimmunoassay (RIA) is now considered a classical and well-known technique for detecting antigens at very low concentrations. It is based upon the competition between radio-labeled and unlabeled antigen for a fixed, limited amount of antibody, as described by R. Yalow and S. Berson in *J. Clin. Invest.*, 39 1157 (1960). The amount of unlabeled antigen influences the distribution of the labeled antigen in antibody-bound (B) and antibody-free (F) labeled antigen, i.e., the more that unlabeled antigen is present, the less the labeled antigen is able to combine with the antibody. In order to obtain conclusive results from the distribution, a good separation between B and F must be made. Methods used for this purpose are, for instance, chromatoelectrophoresis, described by S. Berson and R. Yalow in *The Hormones*, edited by G. Pincus et al, Academic Press, New York (1964), vol. IV, 557, or insolubilization of the antibodies. This insolubilization can be achieved by chemical means (cross-linking or covalent binding to an insoluble carrier) or by physical methods (absorption to an insoluble carrier).

Of the limitations cited above, a most serious limitation until recently has been lack of adequate sensitivity to detect some antigens. In general, three levels of sensitivity are recognizable. Low sensitivity techniques, where materials detected and measured exist in microgram/milliliter quantities, include RID, CF, CEP, CPA, and LPA. Intermediate sensitivity techniques, where microgram/milliliter to nanogram/milliliter quantities of materials may be measured, include HIA, HA, CF, FIA, SIA, VIA, and EIA. Until recently only RIA was able to measure with ultrasensitivity the picogram/milliliter to femtogram/milliliter region.

Many of the techniques listed above require that some form of physically or chemically identifiable label be attached to reagents in the assay system in order that the result of a test can be detected. RIA, FIA, EIA, LIA, VIA, and SIA all fall into this category. Radioactivity, fluorescent moieties, enzymes, complement, viruses, and electron-spin labels are used respectively to generate some form of end-point signal. The sensitivity with which these labels can be detected directly and fundamentally affects the useful ranges of the test systems using them.

The ability to measure the amount or concentration of a label depends upon: (a) the nature of the signal that it generates; (b) the ability of the detector to differentiate the proper signal from the background or interfering signals; (c) the intensity of signal available per unit amount of marker molecule, i.e., the specific activity of the label. With radioactive labels, heretofore the most popular label in use, the signal is decay radiation. Because of the energetic properties of the emissions generated, some of which are penetrating, radioactive decay can be detected easily. Generally, modern counting equipment can be effectively applied to measure the radioactive material. Furthermore, there is a range of specific activities offered by isotopes currently used for tagging.

As noted, up to the present time, the radioimmunoassay (RIA) method in its various forms has been the most sensitive system available. The RIA method, unfortunately, has several serious disadvantages, including the requirement of special equipment, trained staff, the need for extra safety measures to protect against harmful radiation, special licensing, controlled radioactive wastes disposal and the continuous disappearance of labeled compound by radioactive decay. In some instances radiation detection is inefficient. The possibility of replacing the radioactive label with an enzyme label was proposed in 1968 in an article by L. E. M. Miles and C. N. Hales, entitled "Labelled Antibodies and Immunological Assay Systems", *Lancet*, II, 492 (1968), and *Nature* 219, 169 (1968). No procedural details were provided, the article offered only the general idea, leaving it to future workers to determine the basic steps and to perform the extensive experimentation needed to establish a practical operative enzymatic immunoassay method.

More recently, methods for detecting and measuring immunochemical substances have been developed in which, in lieu of a radioactive isotope, immunochemical substances have been labeled with other materials which can be detected by various techniques, e.g., optical and electronic instrument methods. One useful group of materials is enzymes which, because of the great number of analytical permutations, has created a whole family of techniques known collectively as enzyme immunoassay (EIA) techniques.

Among the more recent patents issued that are representative of the state of the art in the detection and measurement of immunochemical substances are, as recited, U.S. Pat. Nos. 3,654,090, issued Apr. 4, 1972; 3,666,421, issued May 30, 1972; 3,791,932, issued Feb. 12, 1974; 3,839,153, issued Oct. 1, 1974; 3,850,752, issued Nov. 26, 1974; 3,879,262, issued Apr. 22, 1975; 4,016,043, issued Apr. 5, 1977; and U.S. Pat. No. Re. 29,169, reissued from U.S. Pat. No. 3,791,932, Apr. 5, 1977, all incorporated by reference herein. See Examples II and III for use of the novel apparatus of our invention in enzyme immunoassays.

A specific example of a recent latex agglutination inhibition method is a qualitative in vitro test for determining the presence of human chorionic gonadotropin (HCG). HCG is a hormone that is characteristic of pregnancy and may be found in the urine of a pregnant human. An antiserum specific to HCG can be prepared from rabbits immunized with HCG to produce the antibody.

According to the PREGNOSTICON ® Slide Test, if the antiserum is mixed with latex that has been sensitized (coated) with HCG, agglutination of the latex occurs. If, on the other hand, the antiserum is mixed with a sample of urine containing HCG, i.e., from a pregnant person, the antiserum is neutralized, and upon subsequent mixing of the antiserum-urine mixture with the HCG-sensitized latex, the agglutination of the latex is inhibited. The latex appears as a milky homogenous suspension, its agglutination having been inhibited. This is a positive test for pregnancy.

Although usually a positive or negative result can be determined by a lack of agglutination or agglutination of the latex, respectively, a maximum inhibition of agglutination may not occur in the early stages of pregnancy when the concentration of HCG in the urine has not increased above a certain threshold level which can be detected by this method. The sensitivity of the described pregnancy test is normally such that the concentration levels of HCG are usually sufficiently elevated by the twelfth day after menstruation fails to occur that the HCG can be detected with the test. If the result of the test is inconclusive, the test must be conducted again in another week or two, to allow sufficient time for an increase in the HCG concentration in the urine to detectable levels. Of course, this is very undesirable from a diagnostic viewpoint, since it is often important to be able to determine the existence of pregnancy at the earliest stages.

The above-described test is qualitative in nature, giving either a positive or a negative test for some threshold concentration of HCG. If HCG is detected in a urine sample, a more quantitative determination of the concentration of HCG in the sample can be made by conducting a series of tests on a series of systematic serial dilutions (commonly referred to in the art as a "dilution series") of the urine samples. Of course, the necessity of conducting a series of tests to determine the concentration of HCG in a single urine sample is time-consuming and costly.

In an available embodiment, the foregoing technique for qualitatively detecting the HCG antigen characteristic of pregnancy is known as the PREGNOSTICON ®-Slide Test (Organon Inc., West Orange, N.J.).

The same general agglutination process principles underlying the PREGNOSTICON ®-Slide Test (and erythrocyte test) can be applied to the determination of other immunochemical substances which can be specifically bound, such as antigens i.e., those associated with gonorrhea (GC), rheumatoid factor (RF), etc., and antibodies such as those specific to GC and RF and so forth.

It is now desirable in the art to provide a test for determining immunochemical substances which would both detect and quantitatively measure the presence of such specifically-bindable immunochemical substances rapidly and at low concentrations, to thereby insure early diagnosis.

There are two types of measuring concepts commonly used in the industry: (a) the first (hereinafter "Concept I"), which employs the concept of light-scattering, including scattering by suspended particles, which block a certain amount of light, so that light which is not absorbed or reflected in a non-detector direction by the particles in what is actually measured (this includes nephelometric methods); and (b) a second, which involves the measurement of the absorption of light by molecules in solutions or "Concept II". Our invention may employ either Concept I or II, but generally employs Concept II.

The use of light-scattering methods of Concept I in analyzing the electromagnetic properties of various substances is well known, and such photometric methods can be used in the analysis of immunochemical substances. There are many different embodiments in which light-scattering Concept I has been used, but, in most cases, the instrumentation required is very sophisticated and expensive. One reason for this is that such instruments typically include a number of lens systems and complicated mechanisms for positioning the cuvette containing the substance being determined, for example, the BRICE-PHOENIX Model OM-2000 Light Scattering Photometer (Virtis Co., Gardiner, N.Y.); SCIENCE SPECTRUM Differential Light-Scattering ® Photometer (Santa Barbara, Cal.). For example, U.S. Pat. No. 3,036,492 issued May, 29, 1962, describes a complex adjustable specimen chamber for determining the light transmittance properties of a sample at varying angles. Another example is U.S. Pat. No. 3,918,817 issued Nov. 11, 1975, which describes a turbidimeter, a particular type of photometer, including a special thermal insulating housing and using a glass test tube of rectangular cross-section. Buffone, "Improved Nephelometric Instrumentation", *Laboratory Management,* April, 1977, describes at page 19 a nephelometer, a similar type of photometer, using an incandescent lamp with filters to produce a band of radiation between 450 and 650 mn.

Much of the literature relating to Concept I has been concerned with textile quality control techniques. For example, textile color analyzers involving instrument head using a plurality of fiber-optic bundles positioned to receive diffuse light reflected from the textile samples have been devised, as described in U.S. Pat. No. 3,986,778 issued Oct. 19, 1976, and U.S. Pat. No. 3,999,860 issued Dec. 28, 1976.

It is interesting to note that Concept I light-scattering photometric agglutination diagnostic methods for determining particular substances have in the past typically required measurement at a particular wavelength, that is, essentially monochromatic light (we believe that these teachings may well be valid to some extent for non-dispersed enzyme immunoassays not requiring the use of particles, but not for agglutination tests).

For instance, in Blume and Greenberg, "Application of Differential Light Scattering to the Latex Agglutination Assay for Rheumatoid Factor" *Clinical Chemistry,* Vol. 21, No. 9, 1975, page 1235 et seq., it is disclosed that in the technique of differential light scattering it is essential that the light source be highly monochromatic, such as, e.g., that produced by a helium/neon-laser (632.8 nm). The requirement of essentially monochromatic light in photometric determinations is again described by Lichenbelt, Pallmarnanobaran, and Wiersema, "Rapid Coagulation of Polystyrene Latex in a Stopped Flow Spectrophotometer", *Journal of Colloid & Interface Science,* Vol. 49, No. 2, 1974, page 281 et seq., and Dininno and McCandless, "Agarose Medium Turbidimetric Assay for Cross-Reacting Antigens", *Journal of Immunological Methods,* Vol. 17, 1977, pages 73-79. See also *Flurometry Reviews, March* 1969 (monthly bulletin of Turner Inc., Palo Alto, CA.

Surprisingly, it has now been found in a major invention by O'Conner in Ser. No. 909,862, filed May 26, 1978, and in a continuation-in-part application thereof (attorney docket OR14200A), filed Aug. 9, 1978, incorporated by reference herein, that for the detection and measurement of overall "average" agglutination of certain insolubilized latex particles in suspension, as opposed to the measurement of the distribution of clump sizes i.e., non-agglutinated or agglutinated latex particles, the requirement for amonochromatic, incident light source is illusory. It has also been found in Ser. No. 909,862 that in agglutination tests the widest spectral band of incident light available, whose upper wavelength limit being equal to or less than the mean diameter of the insolubilized particles in the suspension of interest (the value of which may be expresses herein in nanometers or microns), is preferred for optimum detection and measurement sensitivity. The use of wideband spectral filters, commonly known as low-pass optical filters, in association with an appropriate light source, is indeed unique and novel for the aforementioned applications.

On the other hand, for commercial non-dispersed EIA tests Concept II is made as no particles are employed, and one should use light having a narrow band width centered around the absorbance peak of the substance to be deleted, for example equal to or narrower than 370-430 nm for solutions of the substrate o-phenylenediamine when used with the enzyme alkaline phosphatase.

Testing of agglutination and EIA samples in cuvettes and test tubes has been performed in the prior art in Concept II equipment by complex machinery having optical lens assembles wherein light is passed through the cuvettes from above to detecting means below requiring expensive automated equipment to move the light source from well to well as well as an optical lens assembly. Some systems had great variations on readout because of the optical variations inherent in the measuring small volumes in small test tubes or cuvettes by conventional means. See LABSOURCE RP-800 TM Photometer by PBI Electro-optics Inc., West Westbury, Mass.; FINNPIPETTE TM Analyzer System by Labsystems Oy, Helsinki 81, Finland (a forward-scattering system); Olli 3000 Clinical Chemistry Analyzers TM by Olli Medical Electronics Co., Kivenlahti, Finland; and the Fixed Dual Wavelength Microcomputer Controlled Visible Spectrophotometer by Cooke Laboratory Products, Division of Dynatech Labs Inc., Alexandria, VA. Some concept II attempts have been made using "side-to-side" measurement using low-cost test tubes in colorimeters, such as the SPECTRONIC 20 by Bausch & Lomb (Rochester, N.Y.), which requires a long amount of time for hand insertion and removal of the individual cuvettes, and a large amount of solution to be measured, therefore making measurements of small volumes (i.e., those in microplates) impossible.

To our knowledge the prior art systems did not employ fiberoptic bundles, a reason we now see by hindsight for the necessity of prior art complex systems to either (1) move each cuvette receiving light (and transmitting it to photometer means for detection) relative to a stationary light source means, or (2) move the light souce/light receiving means relative to the stationary cuvette. In either event, economical standard microplates for use in enzyme immunoassay (for example, MICROTITRE ® plates manufactured by Cooke Laboratory Products Div., Dynatech Labs Inc., supra) could not be employed. Visual evaluation of microtitre plates led to subjective and nonreproducible reports of testing. A need therefore existed for an inexpensive manual reader for microplates which would avoid the use of optical lens assemblies and transport systems for light transmission receiving means, would provide a stable readout, and would provide rapid inexpensive evaluation of samples.

In the prior art methods involving the colorimetric determination of liquids using fiber optic probe colorimeter, various [acid resistant and stainless steel or glass] probe tip means has been employed substantially as shown in FIG. 2.

See the Brinkmann Instruments Inc. (Westbury, N.Y.) adapters-Digital probe Colorimeter PC 600D Catalogue, Nos. 20-20-932-1, 20-20-930-5, 20-22-010-4, 20-20-890-2, etc., all requiring contact with the sample medium, so that the tip had to be washed when each sample was tested to avoid contamination, requiring undue testing time. If the probe colorimeter was to be used in the relevant EIA/agglutination art, a need arose to employ a probe tip means of a fiber optic probe colorimeter that could be used to test numerous samples in the wells a microtitre plate quickly and accurately, without washing.

A number of references in distant arts are directed to an optical probe arrangement, employing fiberoptic "light pipes" used in a measuring or testing capacity, c.f. U.S. Pat. Nos. 3,068,742 (Hicks, Jr.); 3,164,663 (Gale); 3,235,672 (Beguin); 3,383,979 (Gibson); 3,493,304 (Rovner); 3,566,083 (McMillin); 3,885,878 et al (Ishak); 3,906,241 (Thompson); and 4,033,698 (Demsky); 4,039,845 (Oberhiinsli). U.S. Pat. No. 3,885,878 and U.S. Pat. No. 4,033,698 both are directed to a measuring apparatus in which suitable fitting or adapter for a positively locating associated fiber optic means is employed. In U.S. Pat. Nos. 3,068,742 and 3,906,241, fiberoptic probes are employed in colorimetric devices. Weinstein in U.S. Pat. No. 3,932,763 discloses a detector for tubular transport articles employing a light beam directed across an opening in a housing, along a path offset from a diameter of that opening. Mudd in U.S. Pat. No. 3,773,426 discloses a device for detecting bacterial growth in a plurality of dilutions wherein a test tray containing a plurality of test wells, each well having a different dilution, is inserted in a frame so that light passes through each well and onto a photo-transistor. If bacterial growth is present in the test well, the light is attenuated, and the drop detected electronically, and punched onto a card. A row of sensors comprising a phototransistor for each of eight dilutions simultaneously reads the samples, light being conducted to each sensor by means of fibre optic bundles. Komarniski in U.S. Pat. No. 3,627,431 discloses a colorimeter wherein a number of samples can be read simultaneously; the instrument incorporates a filter so that the optical density of all samples can be compared on a gray scale. See also U.S. Pat. Nos. 3,518,009 (Shamos); 3,566,083 (McMillin); 3,656,833 (Wallace); 3,773,424 (Selgin); 3,781,092 (Susman); 3,786,266 (Reid); 3,488,156 (Good); and 4,029,391 (French).

It is also interesting to note that recent art complex photometers which have been attempted to be employed for polystyrene microplates in enzyme-linked immunosorbent assays (ELISA) have insisted on employing flat-bottom plates. See E. J. Ruitenberg et al, "Direct Measurement of Microplates and Its Application to Enzyme-Linked Immunosorbent Assay", 3(5) J. CLINICAL MICROBIOLOGY 541–542 (1976).

The preceding discussion illustrates that a need exists for (a) a new improved method and (b) a low cost, simple to use apparatus therefor for making rapid, accurate, and economical measurements of specific binding substances, and in particular, immunochemical substances in emzyme immunoassay agglutination and other colorimetric medical-diagnostic laboratory tests, employing inexpensive disposable microplates having scratches and small defects normally found in the science laboratory.

SUMMARY OF THE INVENTION

The invention relates to the detection and measurement of predetermined, specifically bindable and specific binding substances in agglutination-type test systems or labeled systems (including those immunochemical systems known to those skilled in the art as EIA or FIA) subject to spectrophotometric, colorimetric, or nephelometric analysis, using a novel method and novel combination therefor that provides for rapid an accurate quantitative determinations in an efficient and economical manner. It must also be understood that the invention relates to the detection and measurement of particles by turbidimetry, and to the demonstration and determination, i.e., qualitative and quantitative analysis, of clarity of various non-opaque liquids, whether or not containing suspensions of particles therein.

The colorimeter apparatus may have applications in Concept I optical analytical methods, e.g., for studying molecular and micellar weights of compounds (from about $3 \times 10^2$ to about $10^9$), particle size and size distributions shapes and orientations of macromolecules, interactions in solutions, kinetics of reactions, and polarization of fluoresence, as well as the optical properties of liquids by measuring (as the case might be) turbidity, transmitted light, optical density, depolarization or fluorescence. As will be appreciated by those in the art, it must be understood that qualitative analysis is included in the phrase "detection and measurement" or the equivalent, and that the user, of course, need not at his option utilize the data provided by the method for a quantitative analysis; i.e., "detection and measurement" may be read "detection and measurement, or, if desired, only detection."

In one preferred embodiment of the invention there is provided an optical Concept I method for detecting and measuring in a liquid sample, comprising a suspension of coated particles (preferably latex) particles, the presence and concentration of predetermined specifically bound substance in the sample. By measuring the electromagnetic radiation transmission properties of the sample using a calibrated radiation-measuring combination according to the invention which in this embodiment would utilize a low pass filter eliminating all wavelength above the mean diameter of the particles, the presence and concentration of the immunochemical substance can be determined.

The novel method for analyzing the color of a diagnostic liquid sample located in a microplate well having a predetermined cross-sectional configuration comprises the steps of:

(a) providing substantially uniform light in a predetermined wavelength band from a fiber optic probe colorimeter comprising a light source, a means for detecting and measuring light, and a probe containing a plurality of optic fibers including a first light conducting means for conducting light from the light source of the colorimeter to a test sample and a second light conducting means for conducting light from the test sample to the means for detecting and measuring light of the colorimeter, wherein said probe further includes an attachment means joinable in a close-fitting engagement with an upper portion of said microplate well;

(b) placing said attachment means in close-fitting engagement with an upper portion of said microplate well containing the liquid sample to be analyzed;

(c) passing said substantially uniform light through said first conducting means through said liquid sample in said well to a reflective surface means effectively disposed below said well for reflecting an effective amount of the light passed through said liquid sample back through said liquid sample to a second light conducting means in said probe;

(d) conducting the reflected light through said second light conducting means to said means for detecting and measuring light of said colorimeter; and (e) determining the absorbance or transmittance at a predetermined wavelength band of said liquid sample. Preferably, the substantially uniform light source has a wavelength of from about 400 nm to about 800 nm. By substantially uniform light we mean light uniform in intensity and wavelength range and spectral distribution, so as not to affect the ability of one skilled in the art to determine a value of absorbance or transmittance through a suitable detection means as described herein. More specifically, a colorimetric medical diagnostic method is disclosed for analyzing the absorbance or transmittance at a predetermined wavelength band of a liquid sample located in a microplate well having a predetermined cross-sectional configuration, comprising:

(a) providing substantially uniform light in a predetermined wavelength band from a light source of a suitable probe colorimeter having (1) a first light conducting means for conducting said light to said well, and (2) a second light conducting means for receiving light from said well and conducting said received light to a means for detecting and measuring light of the probe colorimeter, with both light conducting means terminating in a probe tip of uniform cross section surrounded by housing cover means, which covered probe tip is adapted to receive an end cap means having a substantially flat collar with an abutment joinable with said microplate well in a close-fitting engagement, said end cap means engaging the upper portion of said well without engaging said liquid sample, allowing light to be conducted from the first light conducting means to the well and allowing light from the well to be received by the second light conducting means;

(b) placing said end cap means in a close-fitting engagement with the microplate well, and passing the substantially uniform light through said first conducting means through the sample;

(c) providing a suitable reflective surface effectively disposed below said well for reflecting an effective amount of the pass-through light back through the sample to the second light conducting means;

(d) conducting the reflected light through said second light conducting means to said means for detecting and measuring light of the probe colorimeter; and (e) determining the absorbance or transmittance of a predetermined wavelength band of said liquid sample.

The novel combination of the invention for detecting and measuring electromagnetic radiation through diagnostic liquid sample(s) comprises (1) a fiber optic colorimeter comprising a light source, a means for detecting and measuring light, and a probe containing a plurality of optic fibers including a first light conducting means for conducting light from the light source of the colorimeter to a test sample and a second light conducting means for conducting light from the test sample to the means for detecting and measuring light of the colorimeter, and (2) a microplate having one or more wells, each of which is adapted to contain a liquid test sample for use in a predetermined colorimetric medical diagnostic test, wherein a reflective surface is disposed below the bottom of the well of said microplate and said wells are adapted to accommodate the probe of said fiber optic colorimeter, and wherein said probe includes an attachment means joinable in a close-fitting engagement with an upper portion of each well in said microplate without engaging said liquid sample.

Preferably said microplate has from about 96 to about 144 wells. Suitable microplates are manufactured by Cooke Laboratory Products, a Division of Dynatech Labs Inc., Alexandria, Va. under the trademark MICROTITRE ® (which microplates are often called in the trade generically as "microtitre plates"), and by Linbro Scientific Inc., of Hamden, Conn., a division of Flow Laboratories of Rockville, Md. ("LI DBRO ™ plates").

Preferably said means for assuring interfitting attachment comprises a sleeve on said probe, said sleeve having a flange, and said sleeve and flange so constructed to control the location, perpendicularity, and concentricity of said probe with respect to a well of said microplate that accommodates said probe. Said interfitting attachment means is preferably made of plastic or metal, and is preferably stainless steel. The wells of the microplate may have flat (cylindrical) round (hemispherical) or V-bottom (conical) configurations. Contrary to the prior teachings of the enzyme immunoassay art (See, for example, E. J. Ruitenberg et al, "Direct Measurement of Microplates and Its Application to Enzyme-Linked Immunosorbent Assay", 3(5) J. CLINICAL MICROBIOLOGY 541-542 (1976)), we have found that the optic fibers of our invention have transmission characteristics of at least 30% using V-bottom plates at 400 to 900 nm. It is described that the probe terminate with the attachment means to assure a close-fitting engagement. At the termination of said probe (i.e., the probe tip), the optic fibers may be in a random, concentric, or bifurcated parallel axial arrangement. A concentric arrangement is preferable.

Also disclosed is a novel assembly for (1) directly illuminating a liquid test sample located in a microplate well having a predetermined cross-sectional configuration with substantially uniform light provided by a suitable probe colorimeter through a suitable light conducting probe having one end with said colorimeter, and for (2) receiving primarily diffuse reflected light from said sample for analysis in said probe colorimeter, wherein said suitable light conducting probe with the probe colorimeter is comprised of a first light conducting means for transmitting light from the probe colorimeter to the test sample, and a second light conducting means to transmitting the reflected light to the probe colorimeter, with both conducting means terminating in a probe tip end of uniform cross section surrounded by housing cover means, which assembly comprises:

(a) end cap means adapted to slidably receive the covered probe tip end of said light conducting probe, and
  (1) having a substantially flat collar with a suitable abutment means adapted to join the top of the microplate well in sealing engagement, but not to allow the end cap means to contact said liquid sample, and
  (2) allowing light to be transmitted from the first light conducting means to the well, and
  (3) allowing light from the well to be received by the second light conducting means, and
(b) suitable reflective surface means effectively disposed near below or touching the bottom of said well for reflecting an effective amount of the illuminating light to the second light conducting means.

If particles are to be employed (agglutination tests), they may generally be from about 0.20 μm to about 1.3 μm, preferably from 0.40 μm to about 0.65 μm, and most preferably about 0.45 μm, so long as the light source provides radiation of a wavelength below said mean diameter over a wavelength range of at least about 100 nm.

The apparatus of the invention can be operated at ambient conditions of temperature, pressure and humidity in an ordinary light-filled room, and has the advantage of no moving parts and mechanical adjustments that encumbered the prior art.

PREFERRED TYPES OF IMMUNOCHEMICAL TESTS

Figure 1:
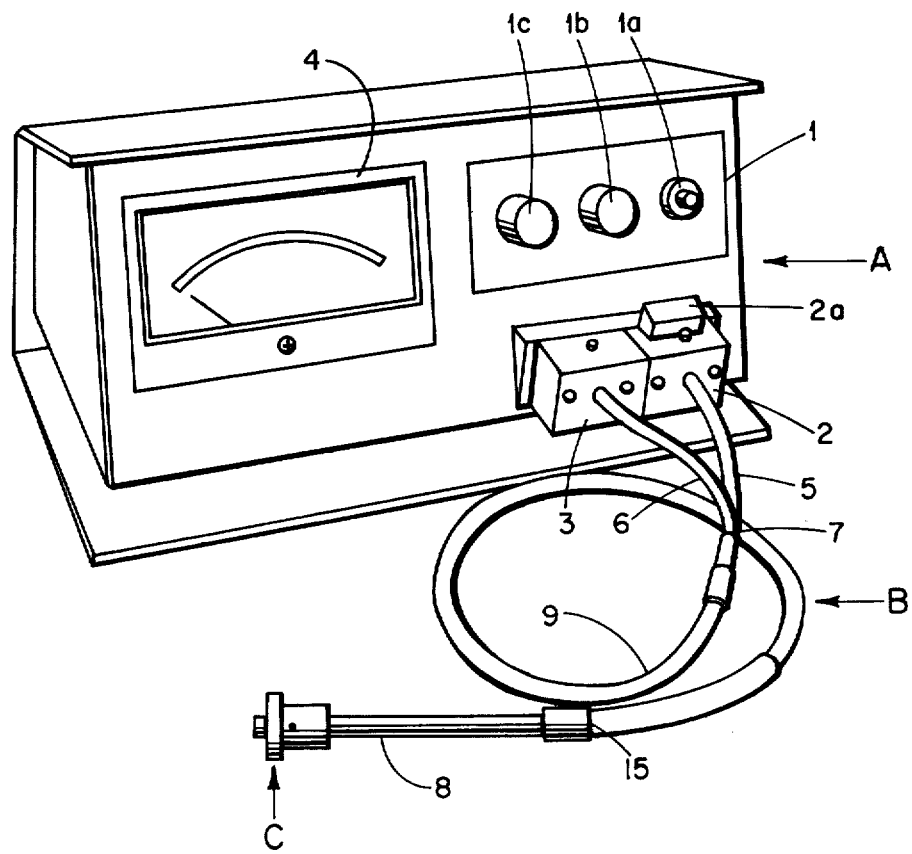
FIG. 1 represents an overall schematic diagram of the novel apparatus according to the invention, without the microplate.
Figure 2:
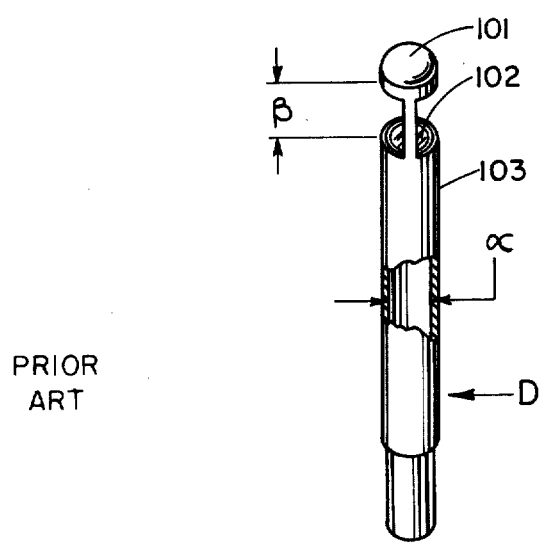
FIG. 2 shows a view of a probe tip means described in the literature that required submersion of the top in the sample to be tested.

While applicable to any labeled system subject to photometric analysis for detection and measurement of the immunochemical substance, the instant invention is preferably applied to any of the insolubilized agglutination and EIA tests commercially available. The latex agglutination tests may be utilized in the methods of Schuurs in U.S. Pat. No. 3,551,555 (1970) and Price et al, U.S. Pat. No. 4,066,744 (1978). Examples of the aforementioned EIA diagnostic tests are represented by Schuurs and co-workers, U.S. Pat. No. 3,654,090 and its progeny as mentioned above.

Enzyme-marked compounds for use in enzyme-immunoassays (EIA) now possess, for most antigens and antibodies to be detected, all of the advantageous properties that were formerly achieved only by radio-immunoassay (RIA): e.g., high specific activity (enzymatic or radioactive), chemical stability, immunologic similarity to the substance to be measured, and chemical purity.

If an EIA technique is employed, the choice of the enzyme which is taken up in the coupling product is determined by a number of properties of that enzyme. It is, of course, essential that the catalytic property of the enzyme should be resistant to the coupling with another molecule. Also of great importance is the specific activity of the enzyme. As less enzyme conjugate is needed to be added to reach a measurable enzyme effect, the sensitivity of an immunoassay system can be increased. With a specified enzyme whose rate of conversion is fixed and whose purity is high, the specific activity of a labeled compound is proportional to the degree of incorporation of enzyme molecules per molecule of marked substance, and a higher specific enzymatic activity results. See German Pat. No. 2,430,356 (1975); German Pat. No. 2,557,419 (1976); U.S. Pat. No. 3,853,987 (1974); Michel F. Aubert, "Critical Study of the Radioimmunological Assay for the Dosage of the Polypeptide Hormones in Plasma", *J. Nuclear and Biological Medicine* 13, 1–19 (1970); Robert Roberts and A. Painter, "Radioimmunoassay for Carrier Creatine Kinase Isoenzymes", *Biochimica Biophusica Acta* 480, 521–526 (1977); Michael G. Grattain, J. M. Puttman, and T. G. Pretlow in "the Use of Glutaraldehyde-Conjugated Horse-radish Peroxidase-Bovine Serum Albumin in the Visualization of Concanavalin A Binding to Tissue Sections of Human Colonic Tumor", *Laboratory Investigation* 35/6, 537–541 (1976), incorporated herein by reference.

Those enzymes can be determined colorimetrically that catalyze a reaction in which a colored substance appears or disappears.

Also, the enzyme should be stable when stored for a period of at least three months, and preferably at least six months at temperatures which are convenient for storage in the laboratory, normally about 4° C. or below.

A product that absorbs light in the ultra-violet region or the visible region, that is, in the range of about 250-750 nm, and preferably 300-600 nm should be either formed or destroyed, directly or indirectly, as a result of the enzyme reaction.

The enzyme should have a satisfactory turnover rate at or near the pH optimum for immunoassay conditions; that is normally at about pH 6-10, and most typically from about 6.0 to about 8.0. Preferably, the enzyme will have the pH optimum for the turnover rate at or near the pH optimum for binding of the antibody to the antigen.

The enzyme which is employed as a label or other enzymes which like activity must not be present in the fluid to be measured, or should be easily removable or deactivated prior to the addition of the assay reagents. Also, one must insure that naturally occuring inhibitors for the enzyme present in fluids to be assayed are not present in concentrations at which they will interfere.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

A summary of properties of enzymes useful for enzyme labels is given below:

1. Available and inexpensive in high purity.
2. High enzymatic specific activity.
3. Soluble under labeling and assay conditions.
4. Chemically and functionally stable under labeling and assay conditions.
5. Enzymatic activity detected simply, sensitively, inexpensively, rapidly and with standard laboratory equipment.
6. Missing or negligible concentration in analyte.
7. Interfering factors missing in analyte.

Enzymes currently used as labeling moieties in enzyme immunoassay (from G. B. Wisdom, *Clinical Chemistry* 22, No. 6, 1243-1255 (1976) are shown in Table I.

TABLE I

Enzymes Currently used as Labeling Moieties in Enzyme Immunoassay

| Enzyme | Source | Enzyme Commission Designation |
|---|---|---|
| Malate dehydrogenase | Pig heart mitochondria | 1.1.1.37 |
| Glucose-6-phosphate dehydrogenase | *Leuconostoc mesenteroides* | 1.1.1.49 |
| Glucose oxidase | Fungal | 1.1.3.4 |
| Peroxidase | Horse-radish | 1.11.1.7 |
| Acetylcholinesterase | Bovine erythrocytes | 3.1.1.7 |
| Alkaline phosphatase | Calf intestinal mucosa and *E. coli* | 3.1.3.1 |
| Glucoamylase | *Rhizopus nivens* | 3.2.1.3 |
| Lysozyme | Egg white | 3.2.1.17 |
| -Galactosidase | *E. coli* | 3.2.1.23 |

Preferably, labelling enzymes generally include catalase, peroxidases, $\beta$-glucosidase, $\beta$-D-galactosidase, $\beta$-D-glucosidase, urease, glucose oxidase, galactose oxidase, and alkaline phosphatase; in general the glucouronidases, galactosidases, ureases and the oxidoreductases. An extremely preferably enzyme is horseradish peroxidase (HRP) which can be obtained relatively inexpensively for pure material, has a high conversion of substrate, and has a substantially flat, fixed rate of conversion.

Use of an enzyme immunoassay system offers attractive advantages: elimination of radioactive substances and their associated hazards and license requirements, common opportunity to use inexpensive laboratory equipment, economical amplification of results through repeated use of enzyme catalysis (a radioisotope atom decays only once) and ready commercial availability of the enzymes. Unlike radioactively labeled compounds where high specific radioactivities lead to increased auto-radiolytic destruction, these high specific enzymatic activity enzyme systems are stable chemically, there being no radioactive emissions present to cause destruction. Hence, preferably markers for the invention are suitable enzymes, with HRP being most preferable.

As known to those skilled in the art, in some instances a "cofactor" or coenzyme, which is a small nonprotein prosthetic group (i.e., compound), is required before an enzyme can exert its catalytic effect on a substrate. An example of such an enzyme is malate dehydrogenase.

The novel method and novel apparatus are also especially suited for agglutination-type immunochemical tests i.e., the so-called latex agglutination tests such as the "NOSTICON" tests mentioned above.

The term "antibody" or "antibodies" as employed herein means a group of serum proteins, also referred to as gamma globulins or immunoglobulins, that will specifically react with an antigen. Most of these antibodies belong to the IgG class, while the other classes are termed IgA, IgM, IgD, and IgE. For convenience, it is also used herein to include what may be classified as certain antigens, to wit, certain naturally occurring specific binding proteins which recognize and specifically bind to certain humoral constituents, for example, proteins such as testosterone, cortisol and thyroxine. These latter commonly called antigens sometimes act as antibodies.

The term "antigen" is employed herein to mean a substance that will react with an antibody. Antigens are often characterized as capable of inducing the formation of an antibody and of reacting with that antibody. However, as will be recognized by those in the art, in the case of "haptens", defined infra, it is necessary to be coupled to a carrier such as, for example, inert absorbing particles, synthetic peptides, or natural protein molecules, in order to induce antibody formation. Materials commonly employed as carriers include, for example, the albumins (human, bovine, or rabbit), synthetic polypeptides (for example, polylysin), inert absorbing particles (for example, charcoal particles) and polymers (for example, dextrans). It is noted that haptens will, in the absence of a carrier, still react with antibodies and can be employed in the antigen-antibody reaction assays of the present invention either with or without carriers.

The term "pure protein" or simply "protein" as employed herein is intended to include proteins and polypeptides that are free of contamination, and it is good practice to use such pure material to avoid necessary interfering factors.

The following Table II lists a partial representation of diseases, causative organisms, antigens, and antibodies within the scope, i.e., detection and determination by the novel method and apparatus of our invention:

TABLE II

REPRESENTATIVE ANTIGENS AND ANTIBODIES
Disease States and Antigen derived from
the Causative Organism or Other Specific
Antigens Used in the Diagnosis of Certain
Disease States I. Infectious Diseases.

| Disease | Organism | Antigen |
|---|---|---|
| A. Parasites | | |
| Amoebiasis | Entamoeba histolytica | Organism sonicate of strain HK-9 |
| Toxoplasmosis | Toxoplasma gondii | Whole organism or their sonicate derived from tissue culture or mouse peritoneal fluid |
| Chagas | Trypanosoma cruzi | Organism sonicate derived from tissue culture |
| Schistosomiasis | Schistosoma haematobium Schistosoma japonicum Schistosoma mansoni | Culture filtrates |
| B. Bacteria | | |
| Infectious meningitis | Neisseria meningitidis | Capsular polysaccharide |
| Gonorrhea | Neisseria gonorrhoeae. | Pili isolated from the bacterial cells |
| Typhoid fever | Salmonella typhi | Bacterial cells or their extracts |
| Pneumonia | Diplococcus pneumoniae | Capsular polysaccharide |
| C. Fungi | | |
| Histoplasmosis | Histoplasma capsulatum | Culture filtrate |
| Blastomycosis | Blastomyces dermatitidis | Culture filtrate |
| Coccidiomycosis | Coccidioides immitis | Culture filtrate |

The novel apparatus and method of the invention can also be employed for the determination of haptens, which may be regarded as a special group of low molecular compounds, and their anti-substances. Haptens and their antisubstances occur most often in low concentrations. As will be recognized by those in the art, and according to the original definition of K. Landsteiner, haptens are protein-free substances whose chemical configuration is such that they can react with specific antibodies, but not such that they are capable of causing the formation of antibodies. In order to be able yet to make antibodies against haptens, the haptens must be coupled to either polypeptides, inert absorbing particles, or natural protein molecules before being injected into a test animal. In the determination of a low molecular weight compound by classical enzyme immunoassy (EIA), the substance to be determined and its enzyme conjugate enter into competition for a given quantity of the antibody. The more unlabeled compound the sample contains, the less the soluble enzyme conjugate of that compound is able to combine with the antibody and the more of the conjugate will remain unbound in the liquid phase. Following a separation of bound and free phases (frequently but not always necessary), the enzyme activity can be measured in a simple manner.

As examples of haptens are mentioned: steroids, such as estrone, estradiol, estriol, cortisol, cortisone, testosterone, pregnanediol, and progesterone; vitamins, such as vitamin B and folic acid; 1-thyroxine; triiodo-1-thyronine; histamine; serotonin; digoxin; prostaglandin; adrenalin; noradrenalin; morphine; vegetable hormones such as auxin, kinetin and gibberellic acid; and antibiotics, such as penicillin.

Hence, the compound or substance to be labeled is a conventional diagnostic material such as a hapten, a drug, a hormone, a protein, nucleic acid or other biologically or immunologically useful or interesting molecule, or viruses or bacteria. If an enzyme marker is chosen and a preference is made to use an insolubilized phase in the reaction scheme, one may adapt the novel method of the invention for a simple "competitive" EIA method (as taught in U.S. Pat. No. 3,654,090), or for a "sandwich" EIA method (as taught in U.S. Pat. No. 4,016,043 or U.S. Pat. No. Re. 29,169, for example), or for a double antibody solid phase "DASP" EIA method (as taught in U.S. Pat. No. 3,839,153). The instantly claimed method and apparatus of the invention can be used with conventional test kits, for example, those kits also set forth in detail in U.S. Pat. Nos. 3,654,090; 3,850,752; 3,838,153; 3,879,262; and 4,016,043. The term "kit" is employed herein to mean a collection of all or some of the chemicals, including the assay tubes or cuvettes, and instructions necessary to do a enzyme immunoassay.

DESCRIPTION OF PREFERRED EMBODIMENTS

The practice of the novel method of the invention involves in each case the determination of the electromagnetic radiation transmission properties of a sample in a microplate using the novel apparatus of the invention.

The apparatus is most conveniently discussed by reference to the drawings, although it is to be understood that the drawings are referred to only for purposes of illustration and example, and the scope of the invention is not limited thereto.

Figure 9:
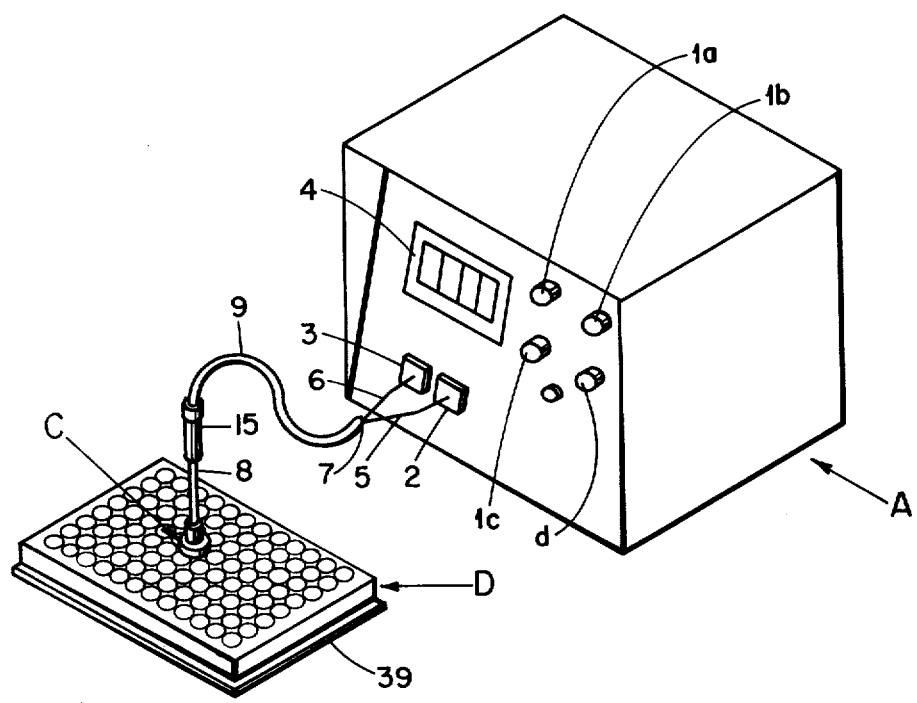
FIG. 9 is an overall schematic diagram of the novel apparatus of FIG. 1, including microplate, in operation.

In FIGS. 1 and 9, apparatus according to the invention are shown schematically. As shown in FIG. 1, the probe colorimeter A is suitably adapted for use with a bifurcated probe B containing a plurality of optic fibers. The probe colorimeter is adapted to incorporate the bifurcated fiber optic bundle at two stations: station 3 (the light transmission station), which transmits a substantially uniform light from a suitable light source within colorimeter A to a first light conducting means 6 of probe B when the latter member is inserted in sealing engagement with station 3. Station 2 is a light receiving transmission station receiving light from the optic fibers within second light conducting means 5 of probe B, and transferring an effective portion of that light after filtration by means of filter 2a to the electrical circuit (detector not shown) of colorimeter A for analyses and a readout of percent transmittance (which can be calibrated and zeroed) in gauge 4. In FIG. 9, the first light conducting member means 6 transmits light from the colorimeter A through the sample in a well through extensions of optic fibers of the first light conducting means in the end of tube 8, a portion of which is transmitted through the sample in microplate D to mirror 39 which reflects a portion of the light from the sample back to extensions of optic fibers of an extension of the second light conducting means in the same end of tube 8 which is transferred back to station 2. The electronic system has various controls 1 (which may include a transmittance zero control 1c, absorbance zero control 1b, power control 1a, etc.) commercially available with the following characteristics:

a. Wavelength from about 400 to about 880 nm.

b. Filters—20 nm half bandwidths at suitable wavelengths, for example, the following center wavelengths for the substrates ortho phenylenediamine, 5-amino salicyclic acid, and azino-di-(3-ethyl-benzothiazoline 6-sulfonic acid) indicated using a commonly employed enzyme such as horseradish peroxidase:

(1) 405 nm
(2) 450 nm
(3) 490 nm
(4) 520 nm

Generally, these filters may be obtained separately.

c. Light source—about 1000 milliwatts per cm or greater.

d. Electrical Requirements—115 Vac, 60 Hz, 220 Vac, 50 Hz.

e. Readout—Meter or digital readout calibrated in 0–100% transmission and absorbance units from 0–2.0.

f. Fiber optic connections—1 connector each at the light source and detector to receive a fiber optic branch of 3/16 -inch diameter.

g. Short-term stability—better than about 0.5% transmittance per day.

h. Long-term stability—better than about 3% transmittance per day.

i. Repeatability—better than about 1% transmittance

The optic fibers themselves are preferably of glass, having, e.g., a wavelength transmission range of about 400 to about 900 nm, or quartz having, e.g., a wavelength transmission range of about 340 to about 880 nm.

A preferred probe colorimeter is the Brinkmann Model PC/600 Colorimeter (Brinkmann Instruments, Westbury, N.Y.) which is designed to accommodate interchangeable filters for a variety of applications and for which additional filters and a battery pack can be obtained separately. Other suitable colorimeters include the Brinkmann Model PC/1000 series (adapted specially with non-standard equipped filters) and Brinkmann CHEMPUTER-3 ™.

Also in FIGS. 1 and 9 is shown the bifurcated probe B has enclosed optic fibers (not shown) traversing each of section 6 (first light conducting means) section 5 (second light conducting means) junction 7, and delivery tube 9. The termination of tube 9 has within it a concentric metal (preferably stainless steel, concentric preferable) tube (FIG. 6) to protect the delicate optic fibers during handling and shipping. Tube 9 is terminated in sealing engagement at junction 15 by a concentric stainless steel fitting 23 through which both transmitting and receiving optical fibers (from both the first and second light transmission means) are routed to a narrow and elongated stainless steel probe sleeve or tube 8, at the end of which the optical fibers are cut so as to have a cross-sectional configuration which is adaptable to fit in novel adapter "C" (to be described below) and hence into microplate "D". A suitable bifurcated probe "B" (or "lightguide") is available through Brinkmann Instruments (Catalogue No. 20-22-110-1 or 20-22-000-7).

Figure 5:
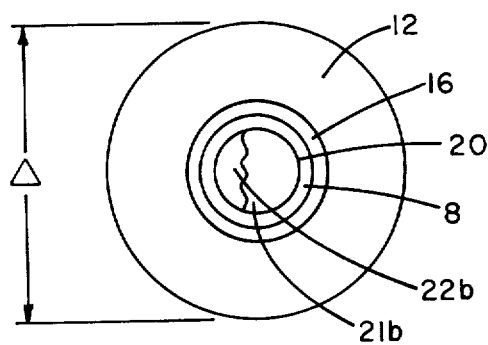
FIG. 5 shows a horizontal section view taken along lines 5—5 of FIG. 4.
Figure 6:
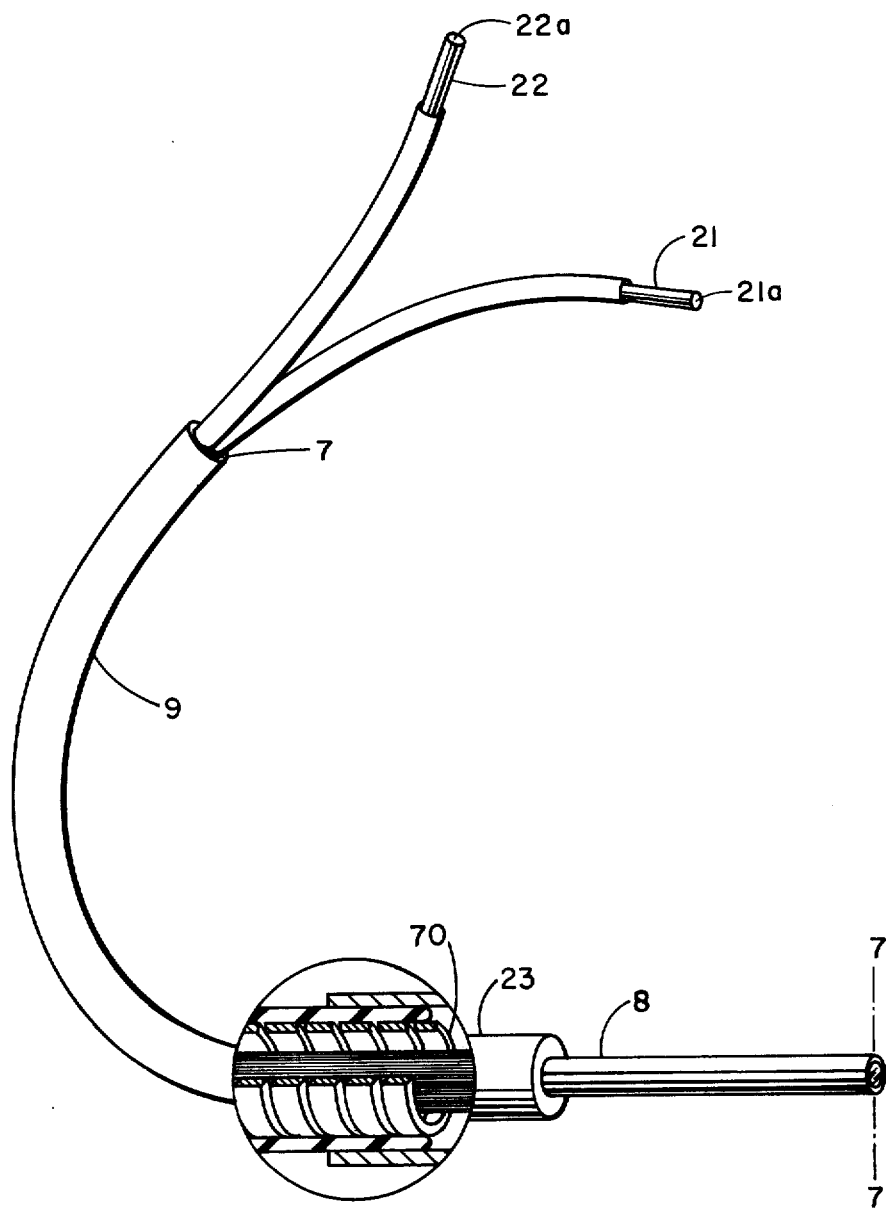
FIG. 6 shows the probe of the colorimeter of FIG. 1 with an axial sectional view of the probe.
Figure 7:
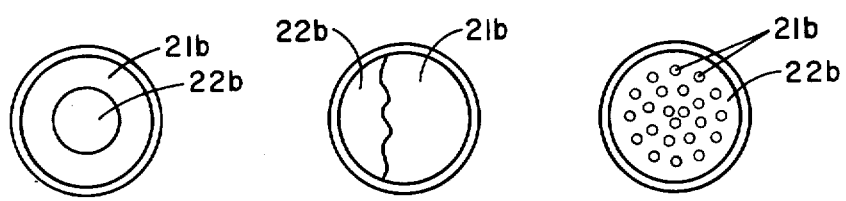
FIG. 7 represents various configurations (concentric, bifurcated and random, as seen from left to right) of optic fibers as seen along lines 7—7 of FIG. 6.

FIGS. 6 and 7 reveal in detail a suitable bifurcated probe "B" for use in the embodiments of FIGS. 1 and 9. FIG. 6 reveals the first light transmission means 6 as having a stainless steel tip 21 concentrically arranged around optic fibers (partially shown) terminating in glass tip 21a for insertion into station 2 of FIG. 1. Similarly, the second light transmission means 5 terminates in glass tip 22a for insertion into station 3 of FIG. 1. The first and second light transmission means 6 and 5 meet at junction 7 are all extended through tube 9 and the metal protecting layer 70 within and joined by a concentric stainless steel fitting 23 molded or welded to a narrow and elongated stainless steel probe tip 8, at the end of which the glass fibers of the first and second means are in one of many possible arrangements, three of which are shown in FIG. 7 (concentric, bifurcated, or random as seen from left to right) with portion 21b representing the extended optic fibers from the first light transmission means, which transmits light from colorimeter "A" to the sample and portion 22b which transmits reflected light from the sample back to the detection apparatus in colorimeter "A" for readout in gauge 4 (FIGS. 1 and 9). The predetermined diameter (slightly less than diameter of the adapter C shown in FIG. 3) of tube 8 is adapted to slidably receive the novel adapter or assembly C shown in detail in FIGS. 3, 4, 5 and 10.

Figure 3:
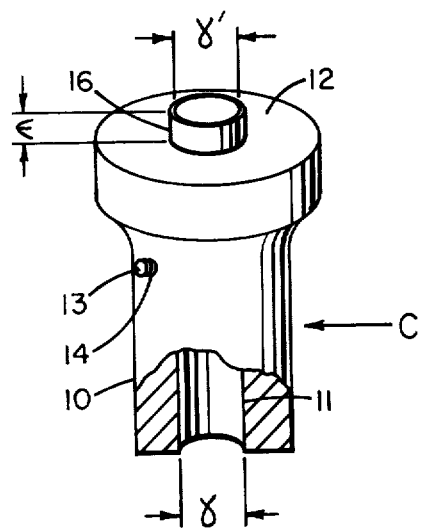
FIG. 3 shows an enlarged view of the novel probe tip adapter apart from the fiber optic probe.
Figure 4:
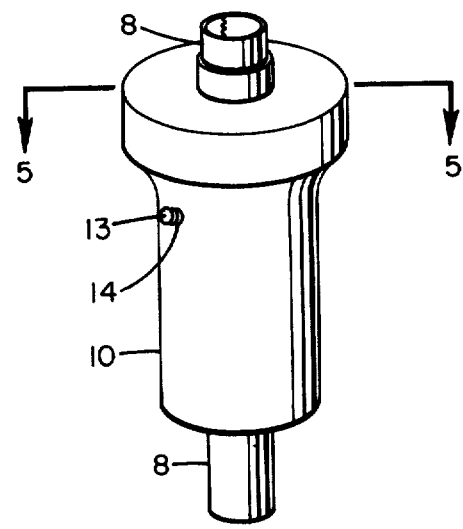
FIG. 4 shows the same probe tip as FIG. 3 but slidably fitted and receiving a section of the fiber optic probe.

In FIGS. 3 and 4, one will note that adapter C is comprised of a cylinder 10 having a hole of internal diameter (here 0.201 inches) adapted to just slidably receive probe tip 8, which may be secured at any predetermined position of an Allen nut 13 which may be screwed in the cylinder 10 via a threaded hole 14. The adapter through Flange 12 is to be located near the terminal edge of tube 8 and is secured to it by tightening the nut prevent the tube 8 from extending so far as to contact or engage the sample in the microplate (see FIG. 10), while at the same time (1) preventing extraneous light (for example, from other wells in the microplate) from reaching the probe tip, and (2) stabilizing the tube 8 and adapter C with respect to the microplate D (FIG. 9) while in use. The sleeve 8 and flange 12 are constructed of metal or plastic so as to control the location, perpendicularity and concentricity of said probe with respect to a well of the microplate that accommodates the sleeves 8 and adapter C.

One will observe in FIG. 5, a horizontal section view taken along lines 5—5 of FIG. 4, that flange 11 is concentric with the extension of cylinder 10 (seen in FIG. 5 as wall 16), as well as with tube 8. The optical fibers 20 in tube 8 may be seen clearly from this position, and a bifurcated arrangement with portions 21b and 22b are shown as a typical arrangement. The ratio of fiber optic bundle area through which light is transmitted to the sample (portion 21b) to the fiber optic bundle area (portion 22b) through which light is received is about 1:1 to about 7:3, and preferably about 7:3.

It is to be emphasized that the extension ε of cylinder 10 is carefully selected so as to be long enough to assume that adapter C will be securely positioned with respect to a given well, while not so long as to engage the liquid sample. The O.D. width of our cylinder 10 is preferably about 0.5". Preferably, the length of the extension is from about 0.060 inches to about 0.100 inches with about 0.90 inch being preferable. The diameter is preferably slightly greater (0.001 to 0.005 inches) than the diameter of sleeve 8, which is preferably about 3/16 inch (0.190 inch) diameter. Diameter $\gamma'$ at the end of the sleeve 8 is preferably slightly less than diameter $\gamma$ (here $\gamma$ is about 0.220 inches). It is therefore emphasized that in diameter of termination of sleeve 8, the internal bifurcated fiber optic bundle (in which the joined end is shown in FIGS. 5 and 7) is never larger than the diameter of the microplate well. The light carrying fibers have transmission characteristics of at least 30% at about 400 to about 900 nm.

When the novel apparatus is in use, metal or plastic adapter C is manually inserted from well to well (see FIG. 9) so as to align concentrically the axis of the well with the axis of the adapter and sleeve 8. The diameter of the flange of the adapter must be enough to completely cover the well and is preferably of at least twice the diameter of the well (here about 0.75 inches). The length of the adapter along the axis of cylinder 10 must be sufficient for a person to be able to hold the sleeve 8 and at the same time maintain the perpendicularity of sleeve 8 with relation to the well/microplate. Preferably, this length of the adapter "C" is at least about three times the width of the well, and preferably about 3.5 times to about 4.0 times (here about 0.96 inches) the width of the well.

Figure 10:
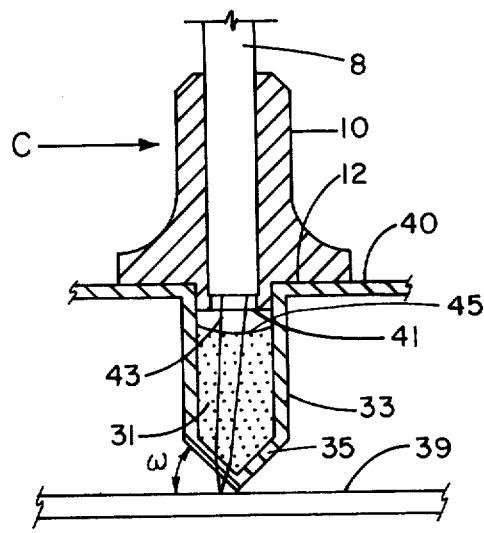
FIG. 10 represents a horizontal sectional view of the novel interfitting attachment means of the invention in sealing engagement with the top portion of a microplate well in operation.

When the novel apparatus is in use as shown in FIG. 10, sleeve 8 is inserted in adapter "C" for which wall 16 of cylinder 10 is comfortably but sealably engages floor 40 surrounding microplate well 31. Wall 33 of well 31 is of sufficient width (here about 0.050 inches) to prevent any substantial amount of light from adjacent wells or environment from entering the well. Preferably, tube 8, cylinder 10 and well 31 are concentrically aligned. Wall 16 (O.D. of cylinder 10, 0.266 inches in extended part) of the extension of cylinder 10 is of the described length (E of FIG. 3) to avoid contact with the surface 45 of the sample within the well but is long enough to provide stable fitting of the adapter C inside the well. Here it is 0.90 inches. Scattered light 43 from the first light transmission member means (not shown) passes through the sample 45 to a mirror 39 and is reflected back to the second light transmission means. Surprisingly, V-bottom (conical) wells are preferably employed, contrary to the teachings of the art (see E. J. Ruitenberg et al, "Direct Measurement of Microplates and Its Application to Enzyme-Linked Immunosorbent Assay", 3 (5) J. Clin. Microbiology 541–542 (1976), and FIG. 8. Preferably a 96 to 106 well microplate is employed here (with wells of about 0.235 inch to about 0.270 inch diameter and depth of about 0.37 inches).

Figure 11:
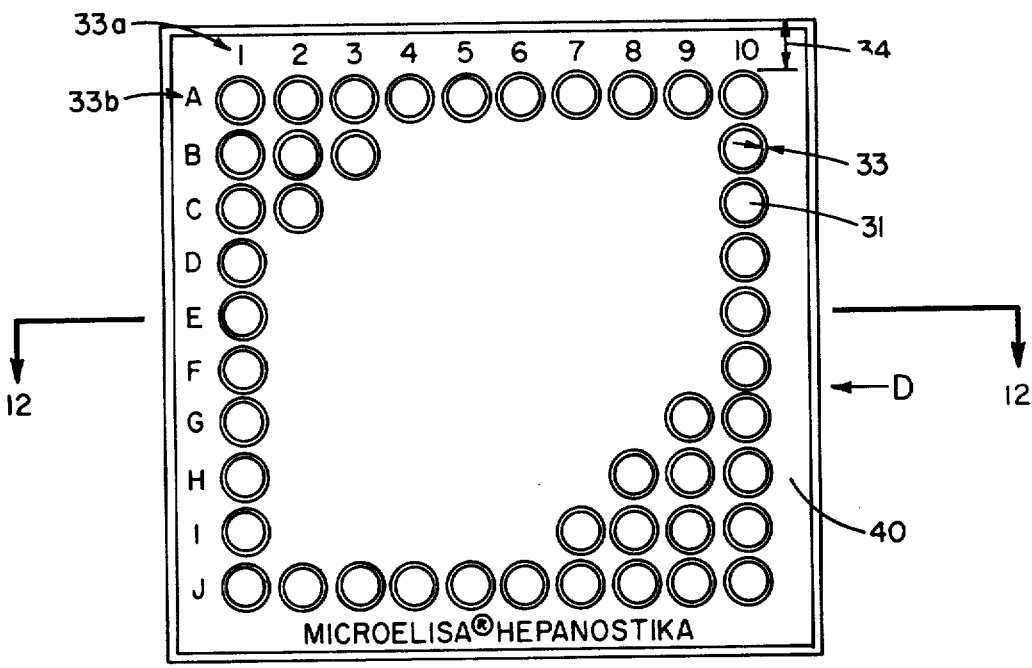
FIG. 11 is a view of a 100 well microplate as shown from above, although a preferred embodiment is a 10×11 microplate (110 wells).
Figure 12:
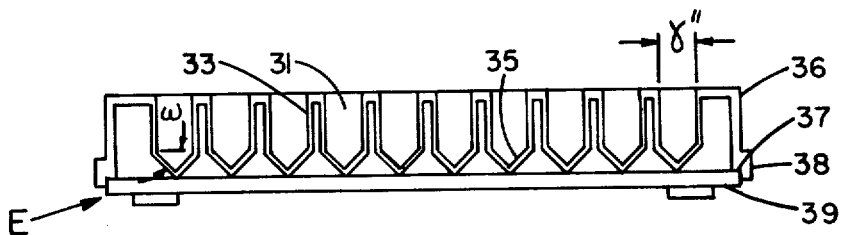
FIG. 12 is a horizontal section view of the microplate as taken along lines 12—12 of FIG. 11.

In FIGS. 11 and 12, a 100 well microplate 40 is shown (MICROTITRE ® Microplate by Cooke Laboratory Products Division, Dynatech Labs Inc., Alexandria, Va., for Organon Inc., West Orange, N.J.) with columns 33a numbered and rows 33b lettered to facilitate easy location and recording of results of a particular sample. The microplate has a sufficient border 34 to accommodate any particular number (33a)-letter (33b) sequence. Each well 31 has walls 33 of sufficient thickness (preferably about 0.050 inch) to prevent any substantial amount of light from entering a well in use by the novel method and apparatus of our invention. The V-bottom walls have an angle ω to the horizontal of 30°–50°, and preferably about 45° with lattice walls 35 about as thick as walls 33. Support 37 of the microplate is adapted with a ridge 38 to receive mirror 39 effectively disposed just below or touching the bottom of the wells of the microplate.

Although the invention has been described with respect to the specific embodiments above, numerous variations and modifications will become evident to those skilled in the art, without departing from the scope and spirit of the invention as described above, defined in the appended claims, and as shown in the following examples:

EXAMPLE I

Various Cooke (MICROTITRE ® microplate with 96 wells custom manufactured for Organon Inc., West Orange, N.J.) and Linbro (Catalogue Model No. 76-221-05 V-Conical-96 well) microplates of "flat" and "V"-bottom configuration were substantially filled with (150 µl in each well) and percent transmission was determined with a Brinkmann Model PC/600 Probe Colorimeter from each of the wells. Each of the above types of microplates was placed over the mirror. The novel adapter "C" of FIGS. 1 and 9 was sequentially placed over each well, and the percent transmission was recorded. The standard deviation and coefficient of variation known to those in the art were determined between wells and plates. A band-pass filter allowing the transmission of light at 490 nm±5 nm was employed for all readings.

| | | No. Plates Measured | No. wells tested per plate | Average Standard Deviation | Average CO-efficient of Var. |
|---|---|---|---|---|---|
| 1. | Well-to-Well variations: | | | | |
| a. | "Flat" Bottom Cooke (MICROTITER ®) | 4 | 32 out of 96 | 6.7 | 9.1% |
| b. | "V" Bottom Linbro 76-221-05 | 15 | 32 out of 96 | 1.66 | 2.5% |
| 2. | Plate-to-Plate "V" Bottom | 15 | 32 out of 96 | 5.3 | 5.2% |
| | A = 490 nm | | | | |

EXAMPLE II

A "competitive" heterogeneous enzyme immunoassay (EIA) method for the detection and determination of thyroxin or "$T_4$" (see U.S. Pat. No. 3,654,090, incorporated herein) in test tubes was employed. The system consisted of the novel apparatus of the invention, antibody coated polystyrene particles, the enzyme horseradish peroxidase (HRP), orthophenylene diamine (OPD), urea peroxide (UP) and citric acid. Briefly, an unknown amount of $T_4$ (sample) and a predetermined amount HRP-tagged $T_4$ are allowed to react competitively with a given amount of polystyrene insolubilized antibody; then excess unknown and HRP-tagged $T_4$ are washed off in the manner described in U.S. Pat. No. 3,654,090, and because of the competitive binding of the sample and enzyme-tagged $T_4$ to the insolubilized antibody, the final reaction of the OPD-UP when allowed to proceed substantially to completion will determine the intensity of the final color, and will be indicative of the concentration of HRP and hence of unknown $T_4$. Citric acid is added to terminate the reaction.

Figure 8:
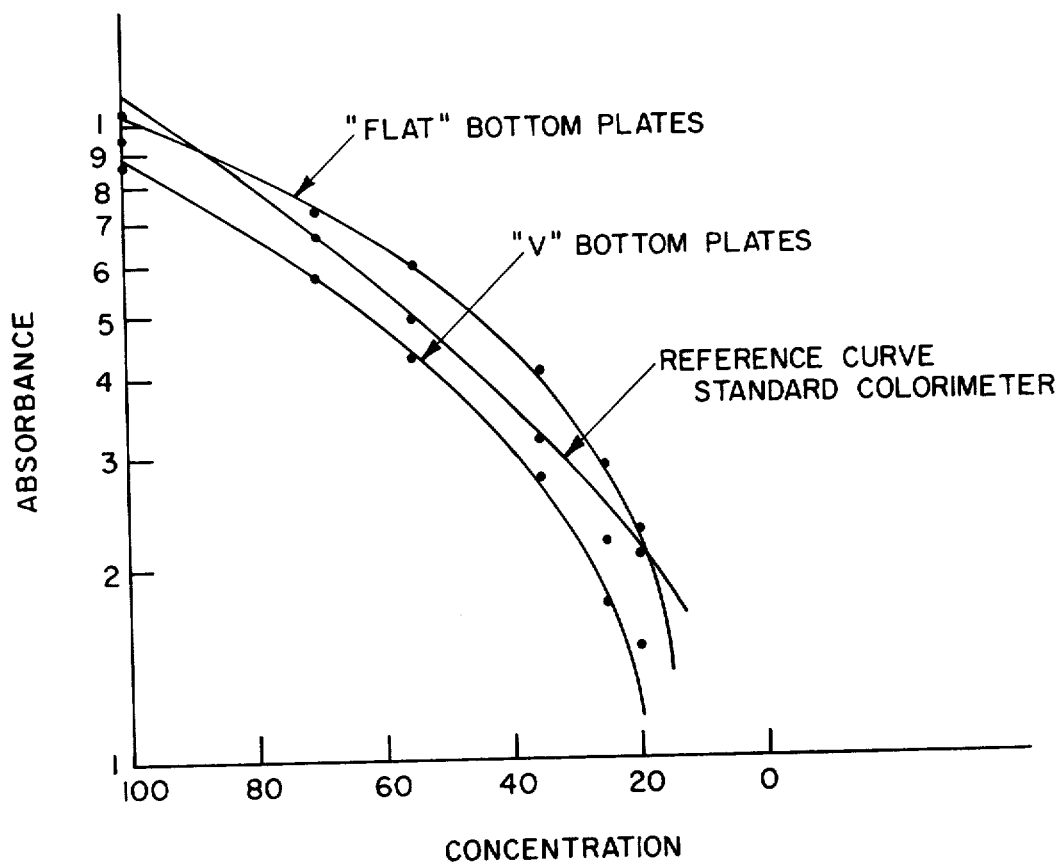
FIG. 8 is a graph illustrating the differentiation of instrument response curves for "flat", "V" bottom, and standard colorimeters (for use in Example III).

After the completion and termination of the reaction, the tubes were centrifuged for separation and 150 µl samples were transferred to "V" bottom plates and read by the novel apparatus of the invention and a Brinkmann Model PC/600 colorimeter and a MICROTITER ® mircoplate. FIG. 8 indicates that the use of the novel microplate adapter and manner in which the reading is performed with microplates is roughly comparable to the method using a standard prior art colorimeter with test tubes.

EXAMPLE III

HEPANOSTIKA ™ (Organon N. V., Oss, the Netherlands) "sandwich" water-insoluble, water-insuspensible heterogeneous enzyme-immunoassay (EIA) tests for the detection of hepatitis were performed (see U.S. Pat. No. 3,791,932, Example III, U.S. Pat. No. 4,016,043, and U.S. Pat. No. Re. 29,169, all incorporated herein) and read with the novel apparatus of our invention.

Each HEPANOSTIKA ™ kit contained:

1. HEPANOSTIKA Test Plates: Five polystyrene plates consisting of 110 wells, MICROTITRE ® V-bottom, each well coated with the gamma globlin fraction of sheep serum containing antibody to Hepatitis B Surface Antigen. Each well is sensitized with 0.1 ml of a solution containing 0.03 mg/ml gamma globulin in 0.04 M Tris-HCl buffer, pH 9.0.
2. HEPANOSTIKA Conjugate: Thirty ampules, 0.5 ml each, gamma globulin fraction of sheep anti-Hepatitis B Surface Antigen coupled to the enzyme, horseradish peroxidase by glutaraldehyde, diluted to an accurately predetermined (by titration) concentraction and freeze-dried.
3. o-phenylenediamine Tablets: Two bottles of ten tablets, each tablet consisting of 12 mg ortho-phenylenediamine-dihydrochloride, 10 mg polyvinylpyrrolidone, 115 mg sodium carbonate (anhydrous), 229 mg citric acid (anhydrous), 50 mg disodium phosphate, 0.2 mg sodium metalbisulphite, 12.8 mg cetyltrimethylammonium bromide.
4. Urea Peroxide Tablets: One bottle of five tablets, each tablet consisting of 41–50 mg hydrogen peroxide; total weight of tablet is 125–155 mg, the remainder consisting of urea and starch.
5. Wash Fluid: Supplied as two bottles of 100 ml each of a tenfold concentrate consisting of 2.0 M Tris-HCl, 2.0 M NaCl, 0.5% polysorbate 80, 0.01% thimerosol.
6. Negative Control Serum: One vial containing 1.0 ml of normal human serum, 7.5 mg glycine and 1.0 mg sodium azide and freeze-dried.
7. Strong Positive Control Serum: One dropper tube containing 0.1 ml normal human serum, 14 ng inactivated Hepatitis B Surface Antigen subtype ad, 14 ng inactivated Hepatitis B Surface Antigen subtype ay, 7.5 mg glycine, 8.1 mg sodium chloride, 1.0 mg sodium azide, and distilled water to 1.0 ml.
8. Weak Positive Control Serum: One dropper containing 0.1 ml normal human serum, 3.5 ng inactivated Hepatitis B Surface Antigen subtype ad, 3.5 ng inactivated Hepatitis B Surface Antigen subtype ay, 7.5 mg glycine, 8.1 mg sodium chloride, 1.0 mg sodium azide, and distilled water to 1.0 ml.

Each HEPANOSTIKA Confirmatory Reagents kit consisted of:

1. HEPANOSTIKA Confirmatory Neutralizing Antibody: Ten dropper tubes, each containing 0.025 ml human scrum with antibody to Hepatitis B Surface Antigen, 0.1 ml normal human serum, 7.5 mg glycine, 8.1 ml sodium chloride, 1.0 mg sodium azide, and distilled water to 1.0 ml.
2. HEPANOSTIKA Confirmatory Control Fluid: Ten dropper tubes, each containing 0.1 ml normal human serum, 7.5 mg glycine, 8.1 mg sodium chloride, 1.0 mg sodium azide, and distilled water to 1.0 ml.

In the preliminary test, unknown samples and controls are added to the MICROTITRE ® plate wells (which have been coated with antibodies specific to hepatitis virus ($HB_sA_g$) and allowed to incubate for the time specified in U.S. Pat. No. 4,016,043. Excess sample and controls are washed, and an antibody specific to $HB_sA_g$ conjugated to HRP is added to the plates and allowed to react for the time specified in U.S. Pat. No. 4,016,043 with the hepatitis virus which is attached to the antisera. The excess HRP is washed away and OPD-UP is added and allowed to react. The intensity of the color reaction is dependent upon the amount of HRP which is attached to the viral particle which may be in the well. Sulfuric acid is added to terminate the reaction. The results show that this application can quantitatively differentiate the various dilutions of a positive sample.

In the HEPANOSTIKA ™ confirmatory procedure, a neutralizing antibody (serum containing the specific antibody) and a control (serum with no specific antibody) is obtained from human serum. A sample of the presumed positive serum is added to 3 wells (A, B, C) and incubated. Then wells A and B are washed as in the preliminary test. Neutralizing antibody to well A and, control to well B is added, and all are incubated for the time specified in the first incubation step of U.S. Pat. No. 4,016,043. Wells A, B, and C are washed, and the remainder of the test proceeds exactly as in the preliminary test, with addition of conjugate.

TABLE II

Differentiation of a Positive HEPANOSTIKA$^{TM}$ Test Sample Dilutions Using the Fiber Optic Probe and Adapter

| Positive Sample Dilutions | Absorbance Readings at 490 nm | Positive to Negative ratio | Result |
|---|---|---|---|
| 10 | 1.4 | 7.14 | pos |
| 10 | 1.4 | 7.14 | pos |
| 10 | 1.4 | 7.14 | pos |
| 10 | 0.45 | 2.31 | pos |
| $10^4$ (1:2) | 0.36 | 1.84 | neg |
| $10^4$ (1:3) | 0.25 | 1.26 | neg |
| $10^5$ | 0.18 | 0.92 | neg |
| $10^6$ | 0.14 | 0.71 | neg |
| negative control | .196 | \ | |
| 1 + control | .310 | 1.58 | |
| 2 + control | .522 | 2.66 | |

Interpretations and Conclusions:
If the specific antigen is present, it will be neutralized by the neutralizing antibody causing a reduced concentration of conjungate available for reacting with the substrate (less color development) when compared to the reaction in wells B and C.
If specific antigen is not present, all wells will be of the same color intensity, i.e.

| | Positive | Negative |
|---|---|---|
| a. If $E_{490}$ Neg Control ≧ 0.050 and a ratio of the positive + controled labeled ≧ 2.1 | If ratio of the sample ≧ 2.1 | If ratio of the sample < 2.0 |
| b. If $E_{490}$ Neg Control ≧ 0.050 and a ratio positive + control labeled < 2.1 | If the ratio of the sample ≧ ratio positive + control | If ratio of the sample < ratio positive + + control |
| c. If $E_{490}$ Neg Control < 0.050 regardless of ratio positive + control | If $E_{490}$ sample > 0.100 | If $E_{490}$ sample ≦ 0.100 |

EXAMPLE IV

In one preferred embodiment of the invention, the immunochemical substance is detected and measured by measuring the electromagnetic radiation properties of a sample prepared using a "competitive" latex-agglutination method, here the PREGNOSTICON ® Slide Test kit by Organon Inc., West Orange, N.J.

Basically, according to the NOSTICON ™ method, a liquid suspension of particles coated with an immunochemical substance having the same immunochemical properties as the immunochemical substance being detected and measured is prepared. The immunochemical substance used to coat the particles may be the identical immunochemical substance being detected and measured. In a preferred embodiment, the particles in suspension are latex particles.

In the PREGNOSTICON ® Slide Test, a latex agglutination-inhibition test, a solution is prepared by mixing a suitable reagent (anti-HCG serum), such as shown below, capable of specifically binding the immunochemical substance within a suitable liquid (urine) as shown below for which it is desired to detect and measure the immunochemical substance.

Then the test solution is combined with the liquid suspension (latex). After allowing sufficient time for agglutination to occur, the electromagnetic radiation transmission properties are determined. The combined reagents, i.e., agglutination reaction, are suitably diluted with an appropriate buffer solution and mixed to facilitate the determination.

The PREGNOSTICON ® Slide Test is a special application of the above NOSTICON ™ method and of an antigen-antibody reaction based on the principle of the Wide and Gemzell Pregnancy Test (*Acta Endocrenologica* 35, 1960), which is designed to demonstrate the presence of human chorionic gonadotropin (HCG) in urine. HCG is the antigen, and serum from rabbits immunized against HCG is the antibody.

According to the method here, polystyrene latex particles having a mean diameter of about 0.45 m are washed in a 0.1 M borate buffer and then exposed to a pre-coating solution of bovine serum albumin. After further borate buffer washing, the latex particles are resuspended in a solution of human chorionic gonadotropin (HCG) and a period of sensitization follows.

The particles here in Example IV were subsequently washed in borate buffer and placed in a final suspension fluid having a pH of 8.2. A dilution of rabbit anti-human chorionic gonadotropin serum was prepared so that in the presence of 1-2 IU HCG/ml (1000-2000 IU HCG/l) contained in a urine specimen, agglutination would be inhibited.

To perform these latex inhibition tests using the novel instrument, 0.05 ml of antiserum dilution was pipetted an mixed in a test tube with 0.05 ml of urine specimen for a period of 30 seconds after which 0.05 ml of the latex suspension was added by pipette and the reaction mixture agitated for two minutes. For pipetting operations, a micropipettor is used, set for 50 μl delivery, with disposable tips. Ten milliliters (10.0 ml) of a 0.1 M borate buffer were added and the test tube contents were mixed by inversion of the covered test tubes two times. A portion of the reaction mixture was then placed in a well of the novel apparatus for readout of the amount of agglutination. Instead of a borate buffer, one may use a phosphate buffer, or a citrate buffer whose ionic strength does not exceed 0.3 M.

In the case of inhibition of agglutination (a positive test for HCG) light transmission will be impeded by the homogeneous suspension; in a negative test, the latex and antiserum will form agglutinates leading to more light transmission through the contents of a well. MI-CROTITRE ® microplates with 110 wells can be used for the novel apparatus of the invention.

EXAMPLE V

This example describes a modification of the GONOSTICON ® DRI-DOT ® latex agglutination test. Polystyrene latex particles having a mean diameter of 0.60 μm are washed in a 0.1 M borate buffer and then exposed to a pre-coating solution of bovine serum albumin. After further borate buffer washing, the latex particles are resuspended in a solution of gonococcal antigen (Gc9) and a period of sensitization follows. This particles are subsequently washed in 0.1 M borate buffer and placed in a final suspension fluid.

To block or neutralize non-specific antibodies found in some human sera, an absorbing antigen prepared by combining the antigens of guinea pig extract and beef erythrocyte stroma is employed.

To perform the modified GONOSTICON ® DRI-DOT ® test using the novel apparatus of the invention, a 0.05 ml sample of human serum to be tested for the presence of gonococcal antibody is mixed in a cuvette with 0.05 ml of absorbing antigen. To this is added 0.05 ml of the GONOSTICON ® sensitized latex. The reaction mixture is agitated for two minutes, and 0.5 ml of 0.1 M borate buffer are added. The covered tube is then inverted twice for final mixing. A portion of reaction mixture was then placed in a MICROTITRE ® well of the novel apparatus for readout.

if agglutination occurs due to the presence of antibody in the sample and its combination with the latex antigen more light will be transmitted; in the absence of gonococcal antibody there will be no agglutination and the homogeneous suspension will impede light transmission through the contents of the cuvette.

EXAMPLE VI

This example describes a modification of the RHEUMANOSTICON ® Slide latex agglutination test. Latex particles are prepared to receive a sensitizing coating of, in this instance, gamma globulin after being washed in a buffer solution, under the same conditions as above. After exposure of the latex to the gamma globulin for a period of time, the latex is washed to remove excess gamma globulin and taken up in a final suspension fluid having an alkaline pH (8.0-8.5).

To perform the modified RHEUMANOSTICON ® Slide test using the novel instrument of the invention, a 0.05 ml of serum sample suspected of having rheumatoid factor (RF) activity is mixed in a cuvette with 0.05 ml of RHEUMANOSTICON ® latex suspension. The reaction mixture is mixed by agitation after which 5.0 ml of glycine buffer of an effective concentration is added. The covered tube is then inverted twice for final mixing and a portion of the reaction mixture is placed in a well of the novel apparatus.

If agglutination occurs due to the presence of RF in the sample and its combination with the latex antigen, more light will be transmitted; in the absence of RF there will be no agglutination, and the homogeneous suspension will impede light transmission through the contents of the tube.

We claim as our invention:

1. In combination, (1) a fiber optic colorimeter comprising a light source, a means for detecting and measuring light, and a probe containing a plurality of optic fibers including a first light conducting means for conducting light from the light source of the colorimeter to a test sample and a second light conducting means for conducting light from the test sample to the means for detecting and measuring light of the colorimeter, and (2) a microplate having one or more wells, each of which is adapted to contain a liquid test sample for use in a predetermined colorimetric medical diagnostic test and each transparent to the light from said first light conducting means, wherein a reflective surface is disposed below the bottom of the wells of said microplate and said wells are adapted to accommodate the probe of said fiber optic colorimeter, and wherein said probe includes an attachment means fittably engaging said probe and joinable in a close-fitting engagement with an upper portion of each well in said microplate to position the probe above the well without engaging said liquid sample.

2. The combination of claim 1 wherein said microplate has from about 96 to about 144 wells.

3. The combination of claim 1 wherein said attachment means for assuring a close-fitting engagement comprises a sleeve on said probe, said sleeve having a flange, and said sleeve and flange constructed so as to control the location, perpendicularity, and concentricity of said probe with respect to each well of said microplate that accommodates said probe.

4. The combination of claim 3 wherein said attachment means is made of metal.

5. The combination of claim 3 wherein said attachment means is made of plastic.

6. The combination of claim 1 wherein the wells of the microplate have flat, round, or V-bottom configurations.

7. The combination of claim 3 wherein said probe terminates within said attachment means for assuring a close-fitting engagement.

8. The combination of claim 7 wherein said probe terminates in a plurality of optic fibers in parallel coaxial arrangement.

9. The combination of claim 7 wherein said probe terminates in a plurality of optic fibers in two bundles having a concentric coaxial arrangement.

10. The combination of claim 1 wherein said optic fibers are glass and have transmission characteristics of at least 30% at about 400 to about 900 nm.

11. The combination of claim 1 wherein said optic fibers are quartz and have transmission characteristics of about 340 nm to about 880 nm.

12. A combination as in claim 1 wherein the reflective surface is a mirror.

13. A method for analyzing a diagnostic liquid sample located in a microplate well having a predetermined cross-sectional configuration, said method comprising:
(a) providing substantially uniform light in a predetermined wavelength band from a fiber optic probe colorimeter comprising a light source, a means for detecting and measuring light, and a probe containing a plurality of optic fibers including a first light conducting means for conducting light from the light source of the colorimeter to a test sample and a second light conducting means for conducting light from the test sample to the means for detecting and measuring light of the colorimeter, wherein said probe further includes an attachment means joinable in a close-fitting engagement with an upper portion of said microplate well so as to position the probe above the well without engaging said liquid sample;
(b) placing said attachment means in a close-fitting engagement with an upper portion of said microplate well containing the liquid sample to be analyzed;
(c) passing said substantially uniform light through said first conducting means through said liquid sample in said well to a reflective surface means effectively disposed below said well for reflecting an effective amount of the light passed back through said liquid sample to a second light conducting means in said probe,
(d) conducting the reflected light through said second light conducting means to said means for detecting and measuring light of said colorimeter; and
(e) determining the absorbance or transmittance at a particular wavelength band of said liquid sample.

14. The method of claim 13 wherein said substantially uniform light has a wavelength of from about 340 to about 900 nm.

15. A probe useful in a fiber optic colorimeter, comprising:
(a) a probe body having a non-colorimeter terminated end;
(b) a first light conducting means for conducting light from a light source of said colorimeter;
(c) a second light conducting means for conducting light to a means for detecting and measuring light of said colorimeter;
(d) a sleeve covering said first and second light conducting means for conducting light;
(e) a probe tip at the non-colorimeter terminated end of said probe body; and
(f) a collar fittably engaging said sleeve in proximity of said probe tip, said collar including a means for producing a close-fitting engagement between said probe tip and a suitable liquid sample containing means to position the probe above the liquid sample containing means without engaging the liquid sample therein.

16. The assembly of claim 15 wherein said microplate well is part of a microplate having from about 96 to about 144 wells.

17. The assembly of claim 15 wherein the covered probe tip contains a plurality of optic fibers in a parallel axial arrangement.

18. The assembly of claim 15 wherein the covered probe tip contains a plurality of optic fibers in two bundles in a concentric arrangement.

19. The assembly of claim 17 or 18 wherein said optic fibers are of glass and have transmission characteristics of at least 30% at 400 to 900 nm.

20. The assembly of claim 17 or 18 wherein said optic fibers are of quartz and have transmission characteristics of at least 30% at 340 to 880 nm.

21. An assembly for (1) directly illuminating a liquid test sample located in a microplate well having a predetermined cross-sectional configuration with substantially uniform light provided by a suitable probe colorimeter through a suitable light conducting probe having one end with said colorimeter, and for (2) receiving primarily diffuse reflected light from said sample for analysis in said probe colorimeter, wherein said suitable light conducting probe with the probe colorimeter is comprised of a first light conducting means for conducting light from a light source of the probe colorimeter to the test sample, and a second light conducting means for conducting the reflected light to a means for detecting and measuring light of the probe colorimeter, with both light conducting means terminating in a probe tip of uniform cross section surrounded by a housing cover means, said assembly comprising:
  (a) an end cap means adapted to slidably receive the covered probe tip of said light conducting probe, having a substantially flat collar with a suitable abutment means adapted to join the top of the microplate well in a close-fitting engagement to position the probe tip above the well without contacting said liquid sample, and further adapted to allow light to be conducted from the first light conducting means to the well and to allow light from the well to be received by the second light conducting means; and
  (b) a suitable reflective surface effectively disposed below said well for reflecting an effective amount of light to the second light conducting means.

22. The assembly of claim 21 wherein the flat collar and abutment of the end cap means are so constructed as to control the location, perpendicularity, and concentricity of said covered probe tip with respect to said microplate well that accommodates said covered probe tip.

23. The assembly of claim 21 wherein said end cap means is made of metal.

24. The assembly of claim 21 wherein said end cap means is made of plastic.

25. The assembly of claim 21 wherein said microplate well has a flat, round, or V-bottom configuration.

26. A colorimetric medical diagnostic method for analyzing the color of a liquid sample located in a microplate well having a predetermined cross-sectional configuration, comprising:
  (a) providing substantially uniform light in a predetermined wavelength band from a light source of suitable probe colorimeter having (1) a first light conducting means for conducting said light to said well, and (2) a second light conducting means for receiving light from said well and conducting said received light to a means for detecting and measuring light of the probe colorimeter, with both light conducting means terminating in a probe tip of uniform cross section surrounded by housing cover means, which covered probe tip is adapted to receive an end cap means having a substantially flat collar with an abutment joinable with said microplate well in a close-fitting engagement, said end cap means engaging the upper portion of said well to position the probe above the well without engaging said liquid sample, allowing light to be conducted from the first light conducting means to the well and allowing light from the well to be received by the second light conducting means;
  (b) placing said end cap on the covered probe tip;
  (c) placing said end cap means in a close-fitting engagement with the microplate well, and passing the substantially uniform light through said first conducting means through the sample;
  (d) providing a suitable reflective surface effectively disposed below said well for reflecting an effective amount of the pass-through light back through the sample to the second light conducting means;
  (e) conducting the reflected light through said second light conducting means to said means for detecting and measuring light of the probe colorimeter; and
  (f) determining the absorbance or transmittance at a predetermined wavelength band of said liquid sample.

27. The method of claim 26 wherein said substantially uniform light has a wavelength of from about 340 to about 900 nm.

28. The method of claim 26 wherein both of said first and second light conducting means contain a plurality of optic fibers.

29. The method of claim 26 wherein the probe tip contains said plurality of optic fibers in a parallel axial arrangement.

30. The method of claim 28 wherein the probe tip contains said plurality of optic fibers in two bands in a concentric arrangement.

31. The method of claim 26 in an agglutination test for the detection of an antigen or antibody.

32. The method of claim 26 in an assay for a specifically bound substance using an enzyme-labeled material.

33. A fiber optic apparatus for optical analysis of a sample, comprising:
  (a) a suitable light source;
  (b) means for detecting and measuring light;
  (c) well means for holding said sample, transparent to the light from said light source, and having a reflective surface disposed beneath said well means;
  (d) a probe located above said well means, containing a plurality of optic fibers, including a first fiber optic light conducting means for conducting light from the light source to a sample and a second fiber optic light conducting means, in coaxial arrangement with said first conducting means, for conducting light reflected by and through said sample to the means for detecting and measuring light.

34. A method for optically analyzing a sample using an apparatus as in claim 33, wherein light conducted to the sample by the first fiber optic light conducting means is transmitted from the probe through the sample to said reflective surface and is reflected back through the sample to the probe, where it is received and conducted by the second fiber optic light conducting means to the means for detecting and measuring light.

35. The apparatus of claim 33 wherein the ratio of the cross-sectional area of the first fiber optic conducting means to the second fiber optic conducting means is from about 1:1 to about 7:3.

* * * * *